(12) United States Patent
Rice

(10) Patent No.: US 8,382,691 B2
(45) Date of Patent: Feb. 26, 2013

(54) ORTHOPEDIC CAST COVER ANCHOR ASSEMBLY AND KIT FOR PROTECTING EXPOSED LIMBS

(75) Inventor: William N. Rice, Atlanta, GA (US)

(73) Assignee: BreakPointe Orthopedics LLC, Atlanta, GA (US)

( * ) Notice: Subject to any disclaimer, the term of this patent is extended or adjusted under 35 U.S.C. 154(b) by 194 days.

(21) Appl. No.: 13/031,630

(22) Filed: Feb. 22, 2011

(65) Prior Publication Data

US 2012/0215144 A1    Aug. 23, 2012

(51) Int. Cl.
*A61F 5/00* (2006.01)
*A61F 5/37* (2006.01)

(52) U.S. Cl. ............... 602/3; 602/22; 128/880

(58) Field of Classification Search .............. 602/3, 5–8, 602/16, 20–22, 32, 62; 128/880; 24/264 R; 2/2.5, 24

See application file for complete search history.

(56) References Cited

U.S. PATENT DOCUMENTS

| 2,596,211 | A | | 5/1952 | Comfort |
| 2,717,437 | A | | 9/1955 | De Mestral |
| 3,263,679 | A | | 8/1966 | Hass |
| 3,487,830 | A | | 1/1970 | Pruett |
| 4,043,326 | A | | 8/1977 | Little et al. |
| 4,139,003 | A | | 2/1979 | Little et al. |
| 4,960,114 | A | * | 10/1990 | Dale ............................ 602/21 |
| 5,980,475 | A | | 11/1999 | Gibbons |
| 6,298,496 | B1 | | 10/2001 | Evans |
| 2003/0191419 | A1 | | 10/2003 | Melin |

* cited by examiner

*Primary Examiner* — Michael Brown
*Assistant Examiner* — Ophelia A Hawthorne
(74) *Attorney, Agent, or Firm* — Eric W. Guttag; Eric W. Guttag IP Law Office

(57) ABSTRACT

An orthopedic cast cover anchor assembly having a cast anchoring member and a coupler member for coupling the cast anchoring member to form a coupled cast anchor assembly in a generally annular configuration. Also, an orthopedic cast cover kit with at least one cast anchoring member, at least one coupler member for coupling the cast anchoring member to form a coupled cast anchor assembly in a generally annular configuration, and at least one limb protective cover which may be releasably fastened to the fastening portion of the cast anchoring member.

26 Claims, 7 Drawing Sheets

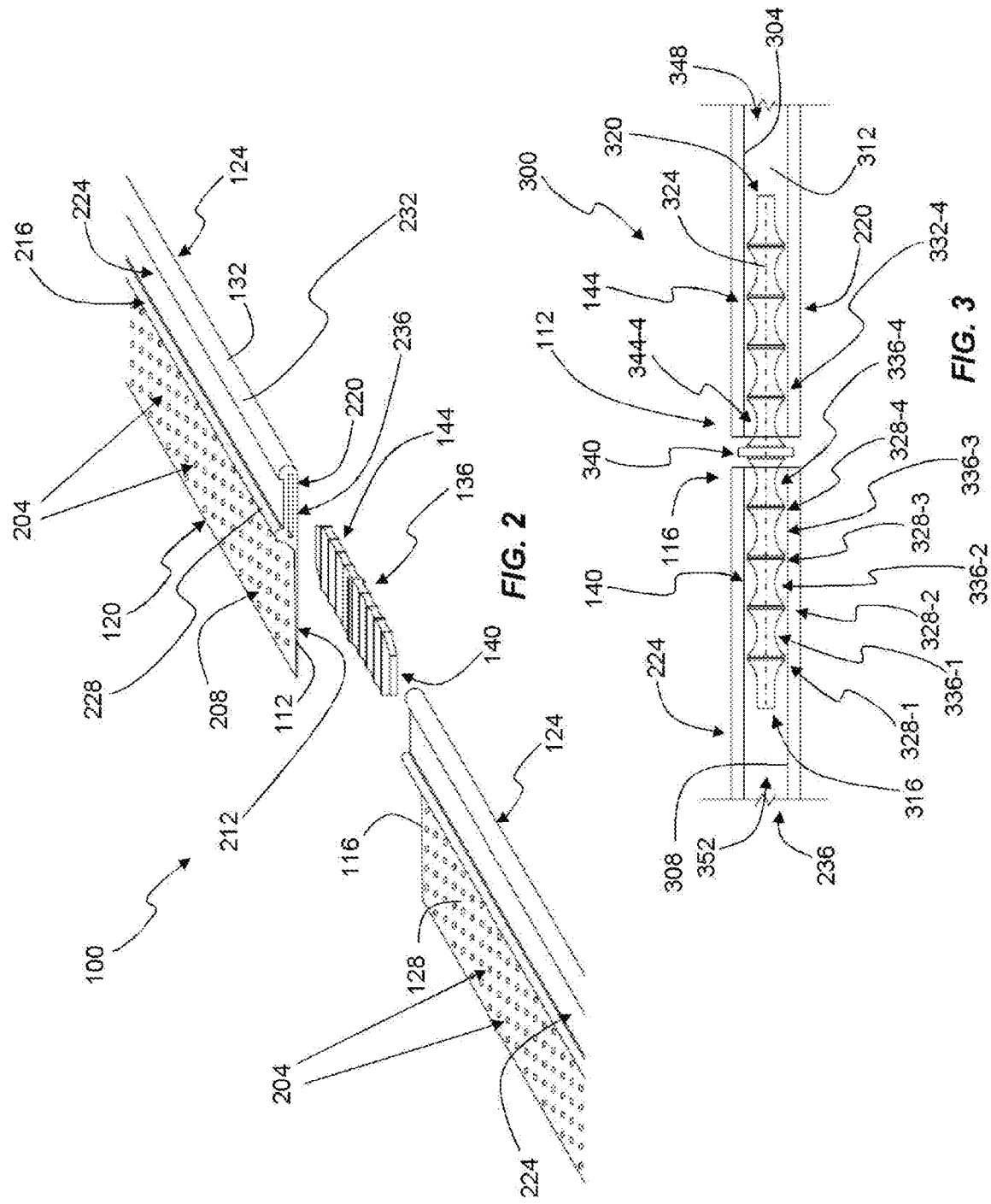

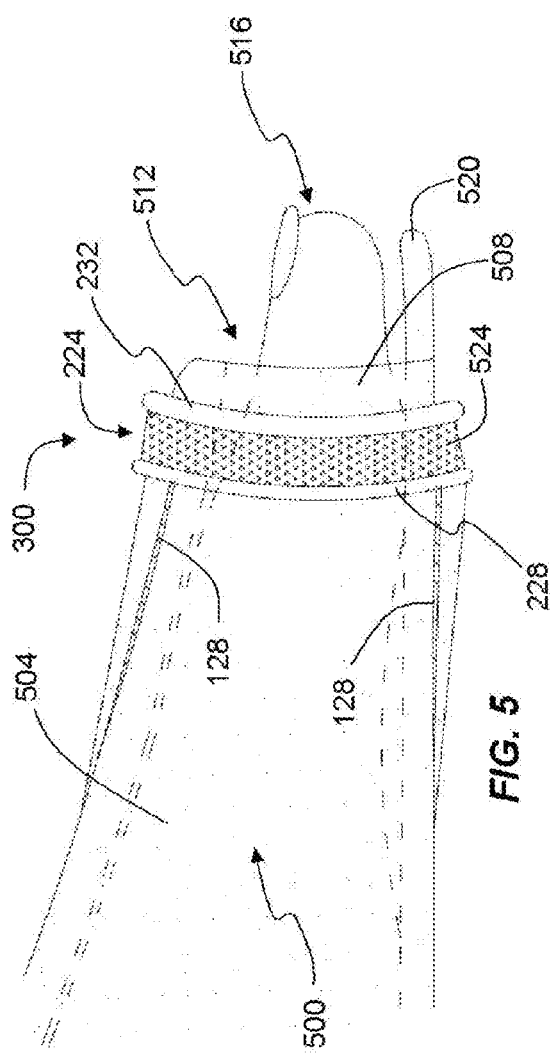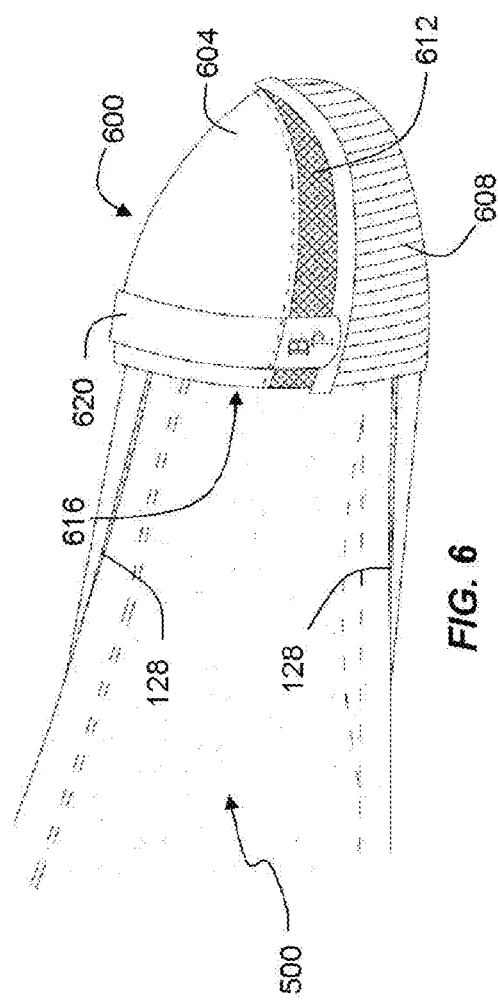

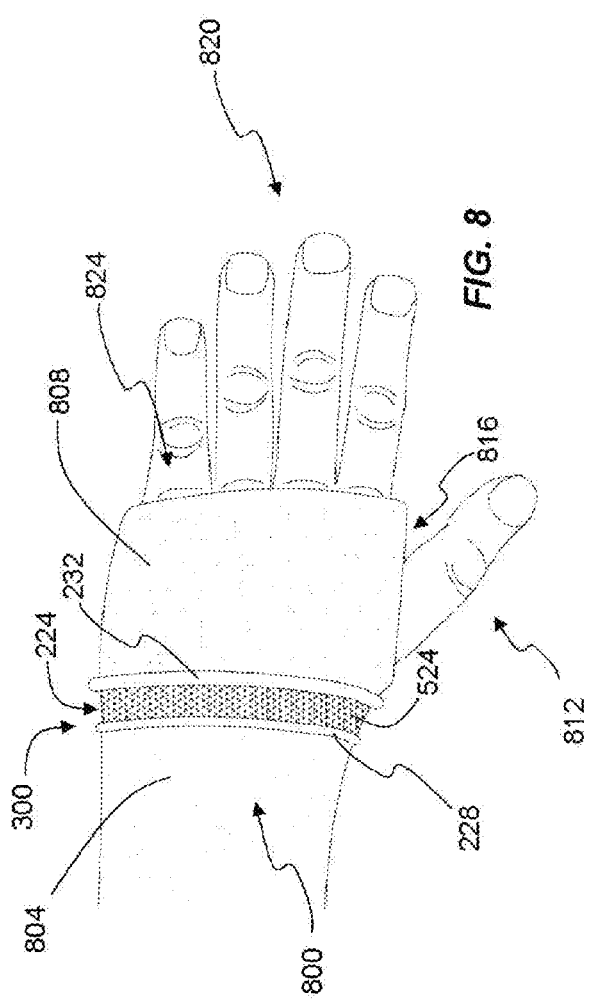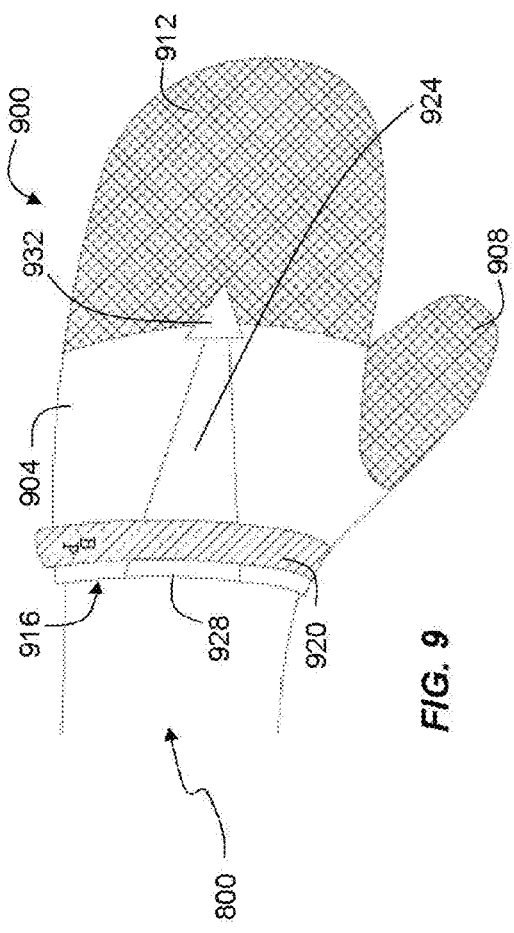

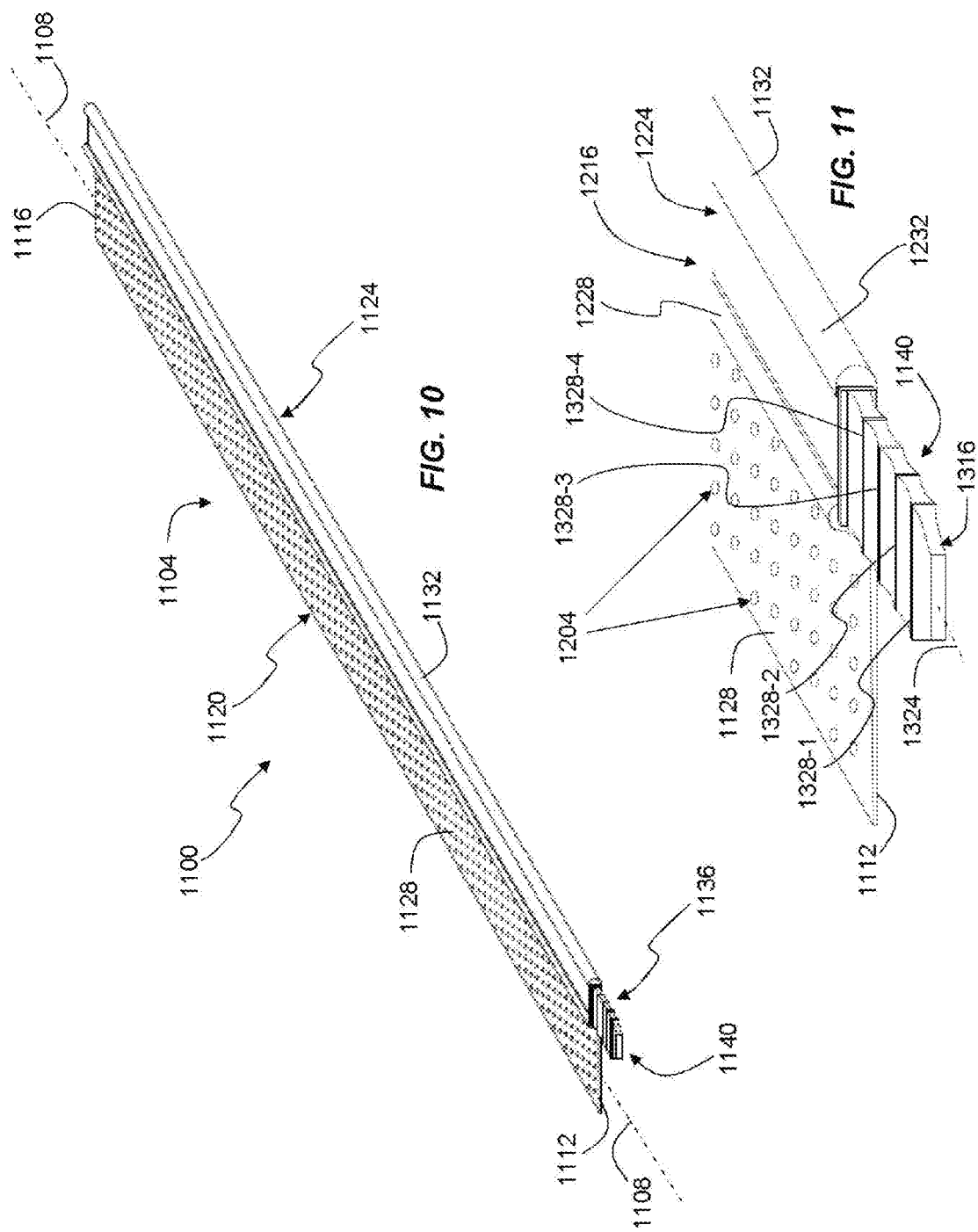

ORTHOPEDIC CAST COVER ANCHOR ASSEMBLY AND KIT FOR PROTECTING EXPOSED LIMBS

FIELD OF THE INVENTION

The present invention broadly relates to an orthopedic cast cover anchor assembly comprising a cast anchoring member and a coupler member for coupling the cast anchoring member to form a coupled cast anchor assembly in a generally annular configuration. The present invention also broadly relates to an orthopedic cast cover kit comprising at least one cast anchoring member, at least one coupler member for coupling the cast anchoring member to form a coupled cast anchor assembly in a generally annular configuration, and at least one limb protective cover which can be releasably fastened to the fastening portion of the cast anchoring member.

BACKGROUND

A person having a broken leg, ankle, foot, arm, wrist, hand, etc., may have an orthopedic cast formed about the broken limb for protection during healing. In the case of casts used for setting limbs such legs, feet, etc., an opening may be left at the forward end of the cast through which portions of the patient's feet, toes, etc., may project outwardly. In the case of casts used for setting broken arms, wrists, etc., portions of the patient's hand, fingers, etc., may also project outwardly. These exposed limbs may subjected to cold temperatures, snow, water (e.g., rain), excessive moisture, excessive sunlight (e.g., UV rays), etc., making the patient uncomfortable. These exposed limbs may also be subjected to further injury, may become soiled or dirty, may present an unattractive appearance, etc.

These exposed limbs projecting from the cast may be covered, protected, etc., with, for example, a makeshift article such as a cut stocking, sock, etc. Such makeshift devices may also present an unattractive appearance. These makeshift devices may also not provide adequate physical protection for the exposed limbs and may also not provide adequate protection and comfort against colder weather, snow, rain, moisture, sunlight, etc. Even when a protective cover is used, such covers may not reliably remain in place when subjected to outside forces or natural stresses during movement by the patient. A limb protective cover which permanently encloses the exposed limb(s) may also not be considered satisfactory because it may be necessary for the physician, doctor, veterinarian, other medical personnel, etc., as well as the patient, to examine the exposed limb(s) occasionally to determine whether blood circulation is adequate, as well as for other medical reasons.

SUMMARY

According to a first broad aspect of the present invention, there is provided an device comprising a orthopedic cast cover anchor assembly comprising:
  an elongated cast anchoring member extending along a longitudinal axis from a first end to a second end and having:
    a pair of spaced apart and opposing side edges;
    a cast securing portion extending along one edge from the first end to the second end for securing the cast anchoring member to an orthopedic cast;
    a cover fastening portion extending along the other edge from the first end to the second end for releasably fastening a limb protective cover to the cast anchoring member;
    a coupler member receiving and securing slot at at least one of the first and second ends; and
  a coupler member having at least one slot receivable and securable portion;
  wherein when the coupler member is received by and secured within the coupler member receiving and securing slot to form a coupled cast anchor assembly, the coupled cast anchor assembly is in a generally annular configuration.

According to a second broad aspect of the present invention, there is provided a device comprising a orthopedic cast cover anchor assembly comprising:
  an elongated cast anchoring member extending along a longitudinal axis from a first end to a second end and having:
    a pair of spaced apart and opposing side edges;
    a cast securing portion extending along one edge from the first cast anchoring member end to the second cast anchoring member end for securing the cast anchoring member to an orthopedic cast;
    an upper cover fastening portion extending along the other edge from the first cast anchoring member end to the second cast anchoring member end for releasably fastening a limb protective cover to the cast anchoring member;
    a lower coupler member receiving and securing slot extending underneath the upper fastening portion and having portions positioned at each of the first and second cast anchoring member ends; and
  a coupler member having a first slot receivable and securable portion and a second slot receivable and securable portion;
  wherein when the first slot receivable and securable portion is received by and secured within the coupler member receiving and securing slot portion at the first cast anchoring member end and wherein when the second slot receivable and securable portion is received by and secured within the coupler member receiving and securing slot portion at the second cast anchoring member end to form a coupled cast anchor assembly, the coupled cast anchor assembly is in a generally annular configuration.

According to a third broad, aspect of the present invention, there is provided a product comprising an orthopedic cast cover kit comprising:
  at least one elongated cast anchoring member extending along a longitudinal axis from a first end to a second end and having:
    a pair of spaced apart and opposing side edges;
    a cast securing portion extending along one edge from the first cast anchoring member end to the second cast anchoring member end for securing the cast anchoring member to an orthopedic cast;
    an upper cover fastening portion extending along the other edge from the first cast anchoring member end to the second cast anchoring member end for releasably fastening a limb protective cover to the cast anchoring member;
    a lower coupler member receiving and securing slot extending underneath the upper fastening portion and having at least one coupler member receiving and securing portion positioned at at least one of the first and second cast anchoring member ends; and
  at least one coupler member having at least one slot receivable and securable portion which may be received by the at least one coupler member receiving and securing slot portion;

wherein when the at least one slot receivable and securable portion is received by and secured within the at least one coupler member receiving and securing slot portion to form a coupled cast anchor assembly, the coupled cast anchor assembly is in a generally annular configuration; and at least one limb protective cover which can be releasably fastened to the upper fastening portion of the cast anchoring member.

BRIEF DESCRIPTION OF THE DRAWINGS

The invention will be described in conjunction with the accompanying drawings, in which:

FIG. 2 is enlarged view of the embodiment of FIG. 1 showing the coupler member and the end portions of the cast anchoring member;

FIG. 3 is a side sectional view of the embodiment of FIG. 1 showing portions of the cast anchor assembly in a coupled configuration;

FIG. 5 is side perspective view of an embodiment of the coupled cast anchor assembly of FIGS. 3 and 4 secured to a leg, ankle, and/or foot orthopedic cast;

FIG. 6 is a similar view to that of FIG. 5, but showing an embodiment of a toe protective cover releasably fastened to the cast anchor assembly;

FIG. 8 is top perspective view of an embodiment of the coupled cast anchor assembly of FIGS. 3 and 4 secured to an arm, wrist, and/or hand orthopedic cast;

FIG. 9 is a similar view to that of FIG. 8, but showing an embodiment of a thumb and finger protective cover releasably fastened to the cast anchor assembly;

FIG. 10 is a perspective view of an alternative embodiment of the orthopedic cast cover anchor assembly of the present invention in an uncoupled configuration; and FIG. 11 is an enlarged view of one end of the alternative embodiment of FIG. 10.

DETAILED DESCRIPTION

Figure 1:
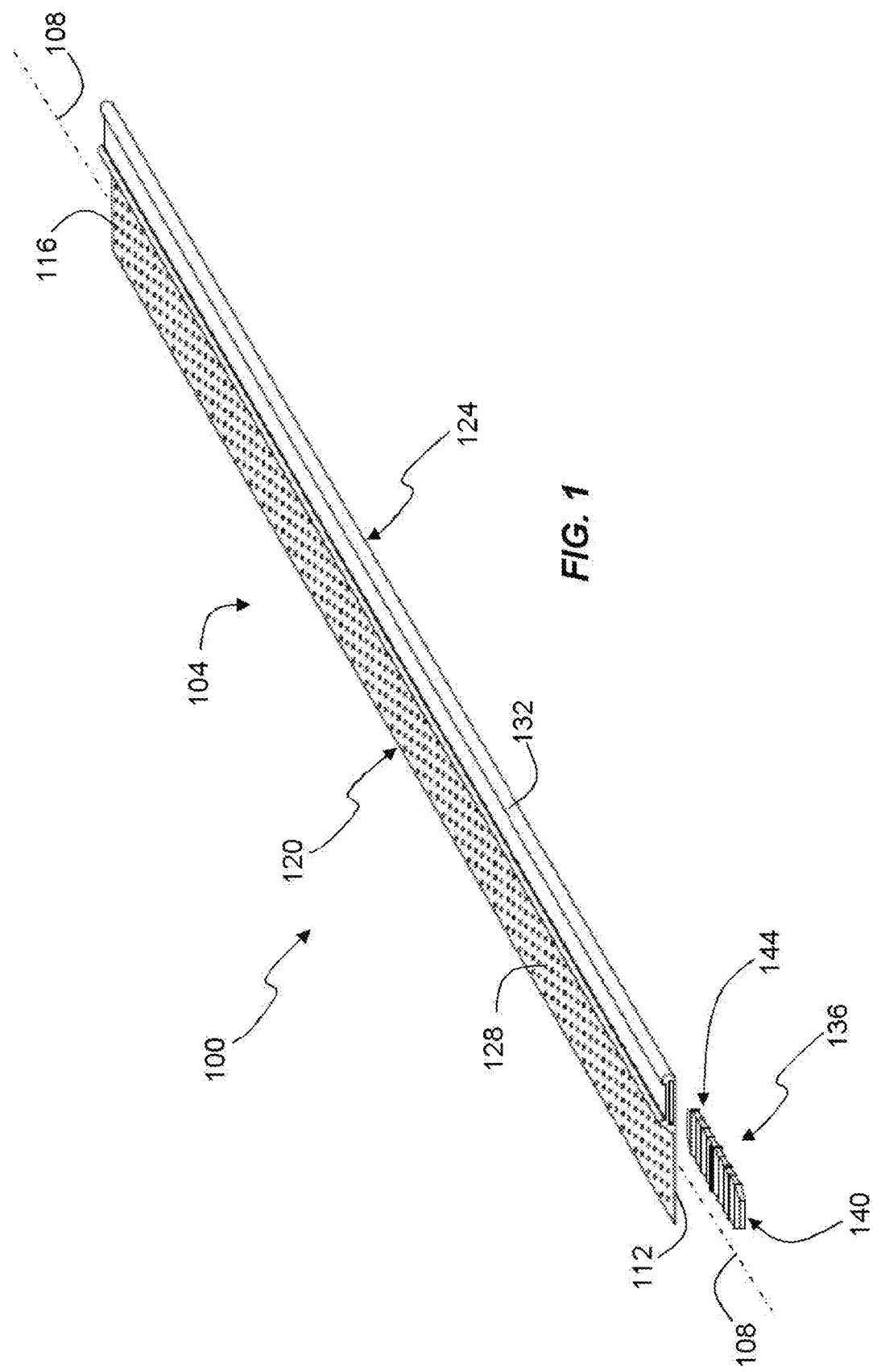
FIG. 1 is a perspective view of an embodiment of the orthopedic cast cover anchor assembly of the present invention in an uncoupled configuration.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically, indicated.

For the purposes of the present invention, directional terms such as "outer," "inner," "upper," "lower," "top," "bottom," "side;" "front," "frontal," "forward," "rear," "rearward," "back," "trailing," "above," "below," "left," "right," "horizontal," "vertical," "upward," "downward," "underside," "outside," "outer," etc., are merely used for convenience in describing the various embodiments of the present invention. For example, the embodiments shown in FIGS. 1 through 11 may be flipped over, rotated by 90° in any direction, etc.

For the purposes of the present invention, the term "orthopedic cast" refers to a cast which may be formed from, for example, bandages impregnated with plaster (e.g., Plaster of Paris/calcined gypsum), fiberglass bandages impregnated with, for example, polyurethane, thermoplastic bandages, one or more pieces of medical tape which may, for example, be layered or laminated together, etc., which is used to set, protect, immobilize a limb (or portion of a limb, for example, in the case of an amputated limb) such as the leg, foot, ankle, arm, hand, wrist, etc., in the case of humans, or, for example, a paw, hoof, etc., in the case of other animals (e.g., dog, cat, horse, etc.), so that the broken, injured, amputated, etc., limb(s) may be permitted to heal.

For the purposes of the present invention, the term "exposed limb" refers any portion of a limb, which may include portions (including amputated portions) of the leg, foot, toes, arm, hand, fingers (e.g., thumb), paw, hoof, etc., which are not covered by the orthopedic cast and which are exposed by, project outwardly from, etc., one or more openings in the cast. The exposed limb may be of a human, or may be of an animal such as a dog, cat, horse, etc.

For the purposes of the present invention, the term "cast anchoring member" refers to the member, device, element, article, etc., of the orthopedic cast cover anchor assembly which is used to secure, attach, embed, insert, implant, set, etc., the cast anchor assembly to, in, etc., the orthopedic cast. The cast anchoring member may be permanently or semi-permanently secured to, attached to, embedded in, inserted in, implanted in, set in, etc., the orthopedic cast. For example, the cast securing portion of the cast anchoring member may be embedded in the orthopedic cast by wrapping one or more layers (e.g., laminating) of the cast forming material over the cast securing portion (e.g., perforated flange 128 as described below) such that the cast anchoring member becomes, for example, unified with the orthopedic cast.

For the purposes of the present invention, the term "cast anchoring portion" refers to that portion or portions of the cast anchoring member which is secured to, attached to, embedded in, inserted in, implanted in, set in, etc., the orthopedic cast.

For the purposes of the present invention, the term "fastening portion" refers to that portion or portions of the cast anchoring member to which the limb protective cover is releasably fastened, attached, tied, secured, affixed, etc.

For the purposes of the present invention, the term "releasably fasten" refers to the limb protective cover being fastened, attached, tied, secured, affixed, etc., to the fastening portion of the cast anchoring member in manner such that the limb protective may also be unfastened, unattached, untied, unsecured, unfixed, etc., from the fastening portion.

For the purposes of the present invention, the term "coupler member" refers to the member, device, element, article, etc., of the orthopedic cast cover anchor assembly which is used to couple, join, link, connect, marry, etc., the cast anchoring member to form the cast anchor assembly in a generally annular configuration. As described below, the coupler member may be separate from the cast anchoring member (see FIGS. 1 and 2), or may be unified or integral with the cast anchoring member, i.e., to provide a unitary cast anchor assembly (see FIGS. 10 and 11).

For the purposes of the present invention, the term "generally annular configuration" refers to the cast anchoring member, when coupled to form the cast anchor assembly, being in a generally circular, oval, elliptical, ring-like, etc., configuration and that generally corresponds in shape to the portion of the orthopedic cast that cast anchoring member is secured to, attached to, embedded in, inserted in, set in, implanted in, etc. See, for example, FIG. 4.

For the purposes of the present invention, the term "limb protective cover" refers to a material, element, device, bandage, dressing, etc., which covers, partially or completely, the exposed limb or limbs, and which may be releasably fastened to the fastening portion of the cast anchoring member. The limb protective cover may be formed from one or more flexible materials, semi-rigid materials, rigid materials, etc., may be hypoallergenic (e.g., latex-free), may include antimicrobial agents, antifungal agents, sterilizing agents, etc., and may protect the exposed limb or limbs against various environmental effects, such as colder (or hotter temperatures), moisture, sunlight (e.g., UV rays), etc., as well as against physical injury of the exposed limb or limbs, provide a sterile protective covering after a surgical procedure (e.g., amputation), allow the medical caregiver to have immediate access to the point of surgery (e.g., sutures, other wound closing devices, etc.) causing additional trauma by, for example, cutting bandages, etc.

For the purposes of the present invention the term "kit" refers to a product, package, etc., which contains at least one (e.g., a plurality or multiplicity of) cast anchoring member, at least one (e.g., a plurality or multiplicity of) coupler member, and at least one (e.g., a plurality or multiplicity of) limb protective cover. The cast anchoring member(s), coupler member(s), and limb, protective cover(s) in the kit may have the same or different configurations, e.g., may be in configurations adapted for use with different size orthopedic casts, may be adapted for use with orthopedic casts for legs, ankles, feet, paws, hoofs, etc., and/or for use with orthopedic casts for arms, wrists, hands, etc., may be adapted for use with orthopedic casts for humans or for veterinary (animal) use, may be adapted for use with orthopedic casts for amputated limbs, etc. In the case of the limb protective covers, these covers may be made of the same or different materials, depending, for example, upon the exposed limb or limbs being protected, may have different patterns of materials, designs, shapes, may be provided in configurations specific for left or right limbs or generally adaptable for left or right limbs, etc.

For the purposes of the present invention, the term "fastening assembly" refers an assembly used to releasably fasten the limb protective coyer to the cover fastening portion of the cast anchoring member. The fastening assembly comprises a complementary pair of fastening elements which includes a first fastening element which is secured to, attached to, formed in, etc., the cover fastening portion, and a second (complementary) fastening element which is secured to, attached to, formed in, etc., the limb protective cover, and wherein, when the first and second fastening elements are joined (e.g., pressed), etc., together, form a temporary connection, link, bond, etc. Fastening assemblies may include, for example, hook and loop fastener assemblies, complementary releasably adhesive surfaces, zippers, snap fasteners, etc.

For the purposes of the present invention, the term "hook and loop, fastener assembly" refers a fastening assembly (e.g., Velcro) which comprises a first element or material (hereafter referred to as the "hook-material") having a "hook" side which may be covered with a multiplicity of tiny "hooks" and a second separate element or material (hereafter referred to as the "loop material") having a "loop" side which may be covered with a multiplicity of even smaller and hairier "loops." When the "hook" side and "loop" side are pressed together, the first and second loops may be a temporarily joined and fastened together, and may thus be separated by pulling the "hook" side and "loop" sides sufficiently and physically apart. See, for example, U.S. Pat. No. 2,717,437 (De Mestral), issued Sep. 13, 1955, the entire contents and disclosure of which is herein incorporated by reference, which discloses the basic "hook and loop" fastening assembly.

DESCRIPTION

Embodiments of the orthopedic cast anchor assembly of the present invention relate to a device which may be incorporated into, attached to, secured, to, embedded in, etc., an orthopedic cast at the time the cast is being constructed, prepared, formed, applied, etc., on the human (or animal) patient's limb or limbs for fastening a limb protective cover over the exposed limb or limbs projecting outwardly from the cast. Embodiments of the orthopedic cast cover anchor assembly of the present invention comprise a cast anchoring member and a coupler member. The cast anchoring member has a cast-securing portion extending along one edge of the cast anchoring member from a first end to a second end along a longitudinal axis for securing the cast anchoring member to the orthopedic cast. The cast anchoring member also has a cover fastening portion extending along the other edge from the first end to the second end for releasably fastening a limb protective cover to the cast anchoring member. When, for example, imbedded into an orthopedic cast, the cast anchoring member (of the cast anchor assembly) may thus provide a permanent (or relatively permanent) mechanism to facilitate the attachment, as well as removal, of a limb protective cover positioned over the human (or animal) patient's exposed limb or limbs.

In one embodiment of the orthopedic cast cover anchor assembly, the cast anchoring member may have a coupler member receiving and securing slot (or portion thereof) positioned at one or both ends of the cast anchoring member. The coupler member may also have one or two corresponding slot receivable and securable portions. The slot receivable and securable portion(s) of the coupler member is received by and secured within the respective coupler member receiving and securing slot(s) (or portion(s) thereof) of the cast anchoring member. The resulting coupled cast anchor assembly is thus formed into a generally annular configuration. In an alternative embodiment of the orthopedic cast cover anchor assembly wherein the cast anchoring member has a coupler member receiving and securing slot positioned at only one end of the cast anchoring member, the coupler member also has only slot receivable and securable portion which is received by the slot. In such an embodiment, the coupler member may be attached to, secured to, etc., to the other end of the cast anchoring member or may be integral with the other end of the cast anchoring member, i.e., the coupler member and the cast anchoring member may form a unitary orthopedic cast cover anchor assembly. See, for example, the embodiment shown in FIGS. 10 and 11.

In another embodiment of the orthopedic cast cover anchor assembly, the cast anchoring member has an upper fastening portion extending along the other edge from the first cast anchoring member end to the second cast anchoring member end for releasably fastening a limb protective cover to the cast anchoring member, and a lower coupler member receiving and securing slot extending underneath the upper fastening portion and having portions positioned at each of the first and second ends. The coupler member has a corresponding first slot receivable and securable portion, as well as a second slot receivable and securable portion, for each of the slot portions positioned at the first and second ends of the cast anchoring member. The first slot receivable and securable end is received by and secured within the coupler member receiving and securing slot portion at the first end of the cast anchoring member, with the second slot receivable and securable end of the coupler member being received by and secured within the second coupler member receiving and securing slot portion at the second end of the cast anchoring member to thus form the coupled cast anchoring member into a generally annular configuration.

The cast anchoring member, through the cast anchoring portion, provides a way, for example, to secure, attach, imbed, insert, etc., the orthopedic cast cover anchor assembly into an orthopedic cast and thus provide a permanent (or semi-permanent) but releasable fastening mechanism to facilitate the attachment and removal of a limb protective cover so that the patient's exposed limb of limbs may be covered, protected, etc., as well as being uncovered when needed, for example, to inspect the exposed limb(s). Embodiments of the orthopedic cast cover anchor assembly may be provided which are sufficiently flexible, adjustable, adaptable, variable, versatile, etc., to be used with orthopedic casts for legs, ankles, feet, etc., with orthopedic casts for arms, wrists, hands, etc., to be used with different sizes of orthopedic casts, etc. Embodiments of the limb protective covers used with this orthopedic cast cover anchor assembly may also be provided which are sufficiently flexible, adjustable, adaptable, variable, versatile, etc., to, for example, keep exposed limbs warm, comfortable, clean, dry, attractive in appearance, etc., even while the patient wears the orthopedic cast for long periods of time. Embodiments of the limb protective covers and orthopedic cast anchor assembly also provide the ability for releasably fastening the limb protective cover to the cast anchoring member so that the physician, doctor, veterinarian, other medical personnel, etc., as well as the patient, may repeatedly and conveniently remove and refasten the limb protective cover to the cast anchoring member without, for example, discomfort to the patient.

The cast anchoring member and coupler member may be easily manufactured in the same or differing sizes from, for example, flexible, pliable, etc., materials. For example, may be formed by extrusion from flexible, malleable, pliable, etc., plastic materials (including are hypoallergenic materials, such as latex-free materials, sterilized or sterile materials, materials treated with antimicrobial agents, antifungal agents, etc.), such as polyethylene, polyester, polyvinyl chloride (PVC), other thermoplastics, etc. The cast anchoring member may also provide the flexibility to be easily sized, cut, etc., to the appropriate, desired, etc., length, shape, configuration, etc., prior to being secured to, attached to, imbedded in, etc., the orthopedic cast by, example, the physician, doctor, veterinarian, other medical personnel, etc. After appropriate sizing, cutting, etc., the ends of the cast anchoring member may be secured together by inserting the receivable/securable portions (e.g., ends or end segments) of the coupler member in the receiving/securing slot or slots (or portions thereof) of the cast anchoring member so that the resulting cast anchor assembly is coupled in an generally annular configuration of the appropriate size, and then secured to, attached to, embedded in, inserted in, etc., the orthopedic cast. In some embodiments of the orthopedic cast cover anchor assembly, the coupled cast anchor assembly may, for example, be laminated in place by wrapping one or more layers of the cast materials over the cast anchoring portion of the cast anchoring member to secure the cast anchor assembly to the orthopedic cast. In some embodiments, the cast anchoring portion (e.g., perforated flange 128 as described below) may be provided with a plurality or multiplicity of perforations, holes, apertures, punctures, etc., to permit the casting material to permeate through cast anchoring portion, thus creating a mechanical unifying joint with the cast forming material such that the anchoring member may be permanently (or relatively permanently) affixed to the orthopedic cast.

The combination of the orthopedic cast cover anchor assembly with the limb protective cover, for example, through the use of a kit embodiment, may provide other benefits to the patient having the orthopedic cast, as well as to the medical personnel who construct, prepare, form, apply, etc., the orthopedic cast to the patient's (or animal's) limb or limbs. For example, the limb protective cover may keep exposed limbs (e.g., toes, fingers, paws, etc.), warm which may increase peripheral circulation in the limb to reduce swelling, thus potentially resulting in faster healing times. Such a reduction in swelling and faster healing may avoid the expense and medical inconvenience of, for example, recasting due to, for example, an ill-fitting or uncomfortable orthopedic cast. A limb protective cover which, for example, covers the open area of a foot or leg orthopedic cast, may assist in keeping the orthopedic cast dry, thus avoiding, retarding, etc., the breakdown of cast forming materials which may be caused by exposure to excessive moisture, as well as protecting the exposed limb(s) against skin diseases, rashes, infections, etc., that may be caused by excessive moisture or other environmental conditions such as athlete's foot or similar fungal infections. The limb protective cover may also provide the ability for the patient, in addition to the medical personnel, to releasably, as well as repeatedly, affix, remove, take off, change, etc., the limb protective cover so that the patient, as well as medical personnel may, for example, inspect the condition of the exposed limb(s), as well as the orthopedic cast, use a different embodiment of the limb protective cover, etc. The limb protective cover may also be provided as an exterior use embodiment (e.g., for use outside of home) and/or an interior use embodiment (e.g., for use at home). For example, the limb protective cover may be provided as interior or sleeping limb protective cover which may be formed of "breathable" materials such as knitted textile to provide the patient with warmth and comfort for limb(s) exposed from the orthopedic cast.

The embodiments of the limb protective covers and cast anchor assemblies of the present invention may be used with human patients (be they adults or children), or for veterinary (animal) patients, (e.g., pets, such as dogs, cats, horses, etc.) For example, in the case of veterinary use, the cast securing portion of the cast anchoring member may be secured by or to the orthopedic cast for an animal by laminating the cast securing portion between layers of tape placed, for example, over fabric stocking, gauze, etc., to prevent the tape from adhering directly to the animals skin, fur, etc., followed by applying layers of cast forming material over the layers of tape.

An embodiment of the orthopedic cast coyer anchor assembly is further illustrated in FIGS. 1 through 4. Referring to FIG. 1, the orthopedic cast cover anchor assembly is indicated generally as 100. Assembly 100 includes an elongated cast anchoring member in the form of, for example, a generally rectangular-shaped anchor band, strap, or strip 104 which extends along a longitudinal axis, indicated by dashed line 108, from a first end 112 to a second end 116. Anchor strip 104 also has a pain of spaced apart and opposing side edges 120 and 124 which may be generally parallel to each other. Extending alongside edge 120 is a cast securing portion in the form of, for example, a relatively planar flange, indicated generally as 128, which may extend as one continuous segment along edge 120 (as shown in FIG. 1) or which may comprise a plurality of separate unconnected (disconnected) segments along edge 120. Extending alongside edge 124 is a protective cover fastening and coupling portion indicated generally 132, which may also extend as one continuous segment along edge 124 (as shown in FIG. 1), or which may comprise a plurality of separate unconnected (disconnected) segments along edge 124. As also shown in FIG. 1, assembly 100 includes a coupler member, indicated generally as 136, which has a first slot receivable and securable portion in the form of, for example, a ribbed slot receivable and securable portion, indicated generally as 140, and a second slot receivable and securable portion, also in the form of a ribbed slot receivable and securable portion, indicated generally as 144 connected to, joined to, etc., first ribbed portion 140.

An embodiment of the orthopedic cast cover anchor assembly is further illustrated in FIGS. 1 through 4. Referring to FIG. 1, the orthopedic cast cover anchor assembly is indicated generally as 100. Assembly 100 includes an elongated cast anchoring member in the form of, for example, a generally rectangular-shaped anchor band, strap, or strip 104 which extends along a longitudinal axis, indicated by dashed line 108, from a first end 112 to a second end 116. Anchor strip 104 also has a pair of spaced apart and opposing side edges 120 and 124 which extend from first end 112 to second end 116 and which may be generally parallel to each other. Extending alongside edge 120 is a cast securing portion in the form of, for example, a relatively planar flange, indicated generally as 128, which may extend as one continuous segment along edge 120 (as shown in FIG. 1) or which may comprise a plurality of separate unconnected (disconnected) segments along edge 120. Extending alongside edge 124 is a protective cover fastening and coupling portion indicated generally 132, which may also extend as one continuous segment along edge 124 (as shown in FIG. 1), or which may comprise a plurality of separate unconnected (disconnected) segments along edge 124. As also shown in FIG. 1, assembly 100 includes a coupler member, indicated generally as 136, which has a first slot receivable and securable portion in the form of, for example, a ribbed slot receivable and securable portion, indicated generally as 140, and a second slot receivable and securable portion, also in the form of a ribbed slot receivable and securable portion, indicated generally as 144 connected to, joined to, etc., first ribbed portion 140.

As also shown in FIG. 2, protective cover fastening and coupling portion 132 comprises an upper protective cover fastening portion, indicated generally as 216, and a lower coupler member receiving and securing portion, indicated generally as 220, which extends underneath upper fastening portion 216. Upper fastening portion 216 is shown in FIG. 2 as having formed therein a recess, depression, indentation, etc., indicated generally as 224, which may be one continuous recess 224 (as shown in FIG. 2) or which may comprise a plurality of separate unconnected recesses 224. Recess 224 also has a pair of spaced apart and opposing shoulders, indicated as 228 and 232. Recess 224 may receive one fastening element of a fastening assembly, for example, one element of a hook and loop fastening assembly which may be either the "hook" material, or the "loop" material. Other fastening assemblies (for example, those involving complementary adhesive surfaces) which are similar to the hook and loop fastening assembly in being formed of a pair of separable but complementary fastening elements which may be temporarily joined, linked, bonded, etc., together may also be used, wherein one of those fastening elements is received by recess 224. In one embodiment, recess 224 may be replaced by a relatively smooth surface to which is affixed (e.g., by adhesive, stapling, bonding, stitching, etc.) one of the fastening elements of the fastening assembly. In another embodiment, recess 224 may be replaced by forming one of the fastening elements permanently along the entire surface (or portions of the surface) of upper fastening portion 216.

Lower coupler member receiving and securing portion 220 has formed therein an elongated coupler member receiving and securing slot 236 having, for example, a generally rectangular cross-section, and which may extend continuously from end 112 to end 116 of anchor strip 104. Providing a continuous slot 236 in portion 220 may make anchor strip 104 easier to manufacture, for example, when using, an extrusion process to form strip 104. In some embodiments, slot 236 need not extend continuously from end 112 to end 116. Instead, slot 236 may comprise a pair of separate unconnected slot portions, one slot portion being formed in lower portion 220 and positioned to open at end 112, while the other slot portion may also be formed in lower portion 220 and positioned to open at end 116 (see FIG. 3).

Figure 4:
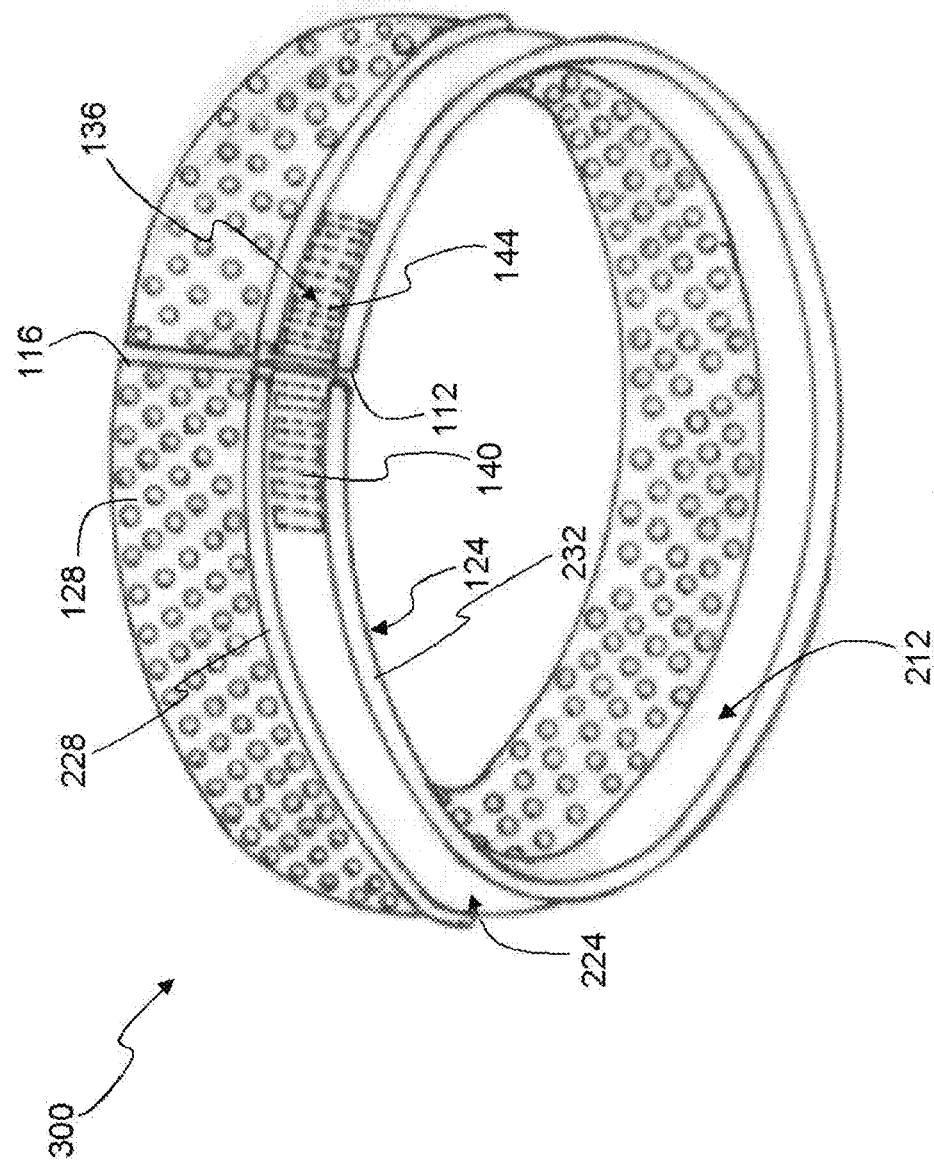
FIG. 4 is a perspective view of the embodiment of FIG. 3 showing the entire cast anchor assembly in a coupled generally annular configuration.

FIGS. 3 and 4 show the orthopedic cast cover anchor assembly in a coupled generally annular configuration (see FIG. 4) indicated generally as 300. Referring to FIG. 3, slot 236 includes one or more walls, for example, an upper wall 304, a lower wall 308, and a pair of side walls, one of which is indicated generally as 312. Ribbed portion 140 has an end segment 316, while ribbed portion 144 has an end segment 320, each of which extend along the longitudinal axis of coupler member 136, indicated by dashed line 324. Each of ribbed portions 140 and 144 also has one or more (e.g., a plurality of) generally oval or elliptical-shaped ribbed segments which protrude outwardly and orthogonally from coupler member longitudinal axis 324 and which are laterally spaced apart along axis 324. Four such ribbed segments 328-1, 328-2, 324-3, and 328-4 are shown and indicated in FIG. 3 with respect to ribbed portion 140, while four such ribbed segments are shown in FIG. 3 with respect to ribbed portion 144, only one of which is indicated as ribbed segment 332-4. (The number of ribbed segments 328 or 334 may be fewer or greater than the number shown in FIG. 3.) Pairs of adjacent ribbed segments 328-1, 328-2, 328-3, and 328-4 may be joined or connected together by corresponding convex connecting segments 336-1, 336-2, and 336-3. As also shown in FIG. 3, coupler member 136 may have a central divider segment 340 which is positioned between ribbed portions 140 and 144, and which is connected to ribbed segment 328-4 by connecting segment 336-4, as well as being connected to ribbed segment 332-4 by connecting segment 344-4.

As also shown in FIG. 3, end segment 316 of ribbed portion 140 is inserted into and fits within end portion 348 of slot 236 which opens at end 116. Similarly, end segment of 320 of ribbed portion 144 is inserted into and fits within end portion 352 of slot 236 which opens at end 112. As end segment 316 is inserted progressively further into end portion 348 of slot 236, the edges of ribbed segments 328-1 through 328-4 (which extend outwardly from axis 324 slightly wider and higher than the width defined by the side walls, such as 312, as well as the height defined by upper and bottom walls 304 and 308 of slot 236) frictionally engage upper and bottom walls 304 and 308, as well as side walls (e.g., side wall 312) of slot 236. In some embodiments, coupler member 136 may be made of a sufficiently pliable, flexible, malleable, etc., material such that the edges of ribbed segments 328-1 through 328-4 deform enough to permit ribbed segments 328-1 through 328-4 to slide within slot 236, yet frictionally engage upper and bottom walls 304 and 308, as well as the side walls (e.g., side wall 312) of slot 236. Similarly, as end segment 320 is inserted progressively into end portion 352 of slot 236, the ribbed segments 332 of ribbed portion 144, such as ribbed segment 332-4, may also deform enough to fit within slot 236, yet also frictionally engage upper and bottom walls 304 and 308, as well as the side walls (e.g., side wall 312) of slot 236.

In other embodiments, the ribbed segments 328 and 332 of ribbed portions 140 and 144 may be made of a relatively rigid material relative to the material that anchor strip 104 is made of. As a result, upper and bottom walls 304 and 308, as well as the side walls (e.g., side wall 312) of slot 236 may be deformed by (yet slidably and frictionally engage) these ribbed segments 328/332 as each of ribbed portions 140 and 144 are progressively inserted into each of end portions 348 and 352 of slot 236. In some of these other embodiments, upper and bottom walls 304 and 308, as well as the side walls (e.g., side wall 312) of slot 236, may be sufficiently soft and pliable such that these slot walls deform to follow (and slidably engage) the contours of ribbed segments 328 and 332, as well as connecting segments 336 and 344, thus providing, for example, a "mechanical pressure" fit.

As shown in FIG. 3, divider ribbed segment 340 is sized so as not to fit within slot 236. Accordingly, as each of ribbed portions 140 and 144 are inserted further within respective end portions 348 and 352 of slot 236, divider ribbed segment 340 eventually abuts against each of ends 112 and 116. This ensures that enough of ribbed portions 140 and 144 fit within each of respective end portions 348 and 352 of slot 236 so that anchor strip 104 (and thus assembly 100) remains in coupled configuration 300. Perforated anchor flange 128 may then, for example, be covered with the casting materials to secure, affix, imbed, laminate in, etc., coupled anchor assembly 300 to the orthopedic cast permanently or semi-permanently so that assembly 300 does not separate from (i.e., remains unified with) the orthopedic cast.

Divider ribbed segment 340 may also serve the additional function of providing a resistance point for inserting each of ribbed portions 140 and 144 into the respective end portions 348 and 352 of slot 236, thus making coupling (or even uncoupling) of anchor strip 104 easier to accomplish. For example, ribbed portion 140 may be first inserted into end portion 348 of slot 236 until divider segment 340 abuts end 116. Then, ribbed portion 144 may be inserted into end portion 352 of slot 236 until divider segment 340 also abuts end 112, thus signifying that anchor strip 104 is in coupled configuration 300. Once in coupled configuration 300, anchor strip 104/assembly 100 generally remains in that coupled configuration while being secured to, attached to, embedded in, etc., the orthopedic cast. But because the edges of ribbed segments 328 and 332 of each of ribbed portions 140 and 140 which frictionally engage upper and bottom walls 304 and 308, as well as side walls (e.g., side wall 312) of slot 236 may be deformable in some embodiments (or in alternative embodiments, anchor strip 104 may be soft and pliable), anchor strip 104 may also be uncoupled, if desired or needed, by simply pulling ends 112 and 116 apart with sufficient force (and physical manipulation of coupler member 136 and anchor strip 104) until one or both of ribbed portions 140 and 144 come out of respective end portions 348 and 352 of slot 236.

Figure 7:
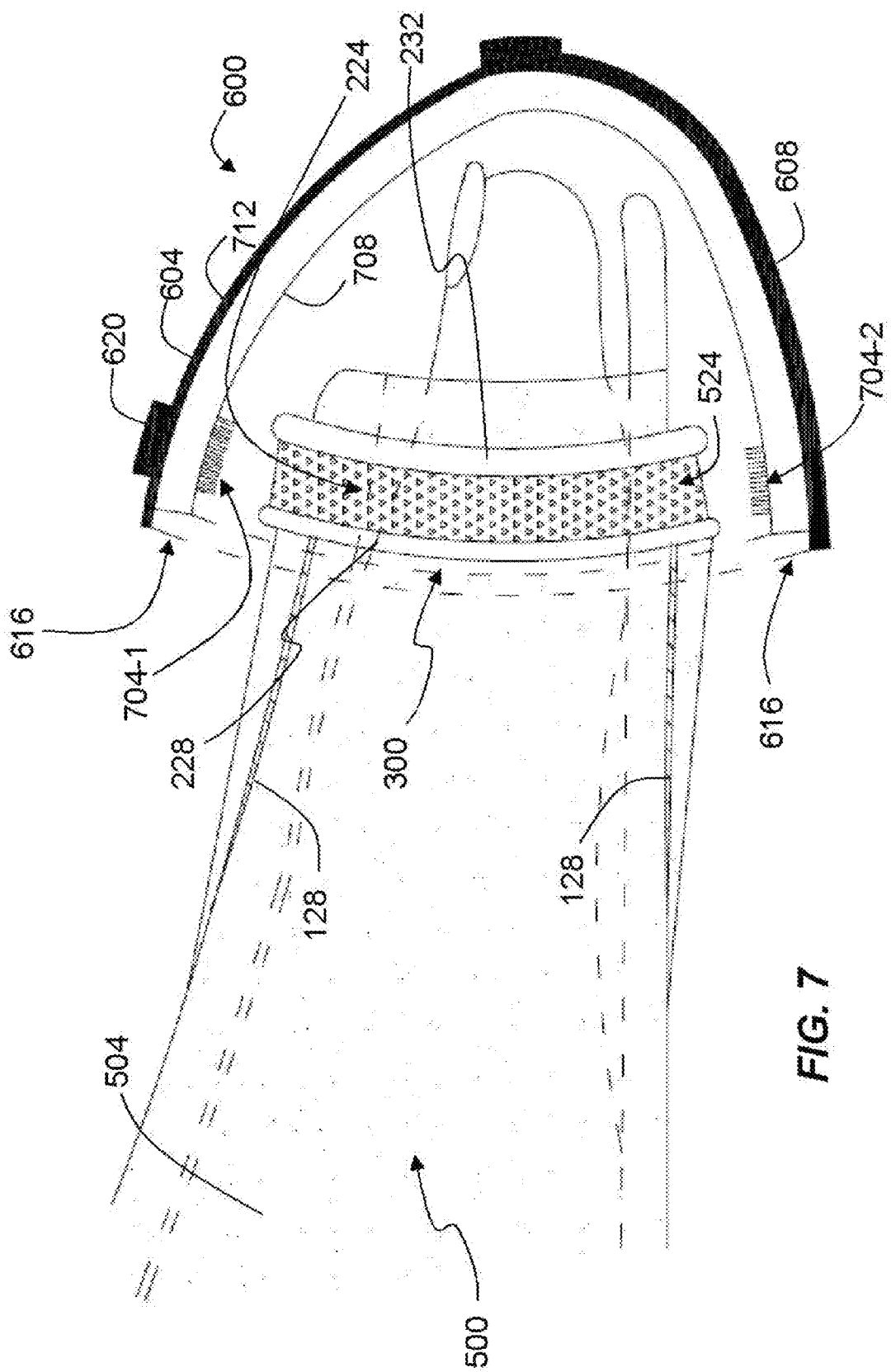
FIG. 7 is a similar view to that of FIG. 6, but also providing a sectional view of the embodiment of the toe protective cover to illustrate how the toe protective cover is releasably fastened to the cast anchor assembly.

FIGS. 5 through 7 show an embodiment of coupled anchor assembly 300 secured (embedded) in a leg, ankle, or foot cast, indicated-generally as 500, via perforated flange 128. (Although FIGS. 5 through 7 show an embodiment of coupled anchor assembly 300 secured to (e.g., embedded in) a left leg, ankle, or foot, cast 500, assembly 300 may also be similarly secured (e.g., embedded in) a right leg, ankle, of foot cast 500.) Referring to FIG. 5, coupled anchor assembly 300 is positioned and secured between the main or rearward leg/ankle portion 504 and the forward or toe portion 508 of cast 500. Coupled anchor assembly 300 is also shown positioned proximate or adjacent to opening 512 in forward portion 508 of cast 500 from which the patient's exposed toes, indicated generally as 516, project outwardly from forward portion 508. As also shown in FIG. 5, bottom portion 520 of cast 500 (which may alternatively be a foot plate which may or may not be an integral part of cast 500), projects outwardly beyond opening 512 and underneath toes 516. As further shown in FIG. 5, recess 224 is provided with one fastening element, indicated generally as 524, of a limb protective cover fastening assembly, for example, the "hook" material or "loop" material of a hook and loop, fastening assembly. Fastening element 524 may be a continuous strip of material, as shown in FIG. 5, but may also be provided as a plurality of separate disconnected segments of sufficient number and length to provide adequate fastening capability.

Referring to FIG. 6, a left-footed toe protective cover is provided, which is generally indicated as 600. The embodiment of toe protective cover 600 shown in FIG. 6 comprises an upper portion, indicated generally as 604, a lower portion, indicated generally as 608, and an intermediate portion, indicated generally as 612, joining upper portion 604 and lower portion 608. (For a right-legged cast 500, a right-footed embodiment of the toe protective cover 600 which is correspondingly configured may be used with such a right-legged cast 500.) Upper portion 604, lower portion 608, and intermediate portion 612 may be made from a variety of materials (e.g., for comfort such as warmth, for protection such from moisture, sunlight, UV ray, etc., for washability, etc.), may be formed in a variety of patterns or designs, etc. For example, upper portion 604 may be made from, for example, a breathable woven textile, (for example, made from a breathable, yet water resistant/waterproof material, natural or synthetic fur or fur-like materials, leather, suede and synthetic suede, etc., may be decorated with stones, artwork, designs, logos, etc. This upper portion 604 may be attached to intermediate portion 612 in the form of, for example, an elastic insert which is joined or attached to bottom portion 608 which may be, for example, in the form of a "rubber" or "rubberized" bottom or sole (e.g., made of a water protective or resistant material). Toe protective cover 600 may also be made in different sizes, may be provided in different configurations to fit left or right feet, etc. The open rearward end of toe protective cover 600 is indicated by arrow 616. As also shown in FIG. 6, toe protective cover 600 may be provided with a fit adjusting strap 620 which allows, the patient to tighten, or correspondingly loosen, the fit of cover 600 over coupled anchor assembly 300. Strap 620 may also be used as decorative feature (e.g., include the manufacturer's logo, etc.) which, for example, may be used to embellish, hide, etc., the sewing or stitching used to secure the fastening element complementary to element 524, and which is present on the underside of cover 600, as described below. Fit adjusting strap 620 may also be releasably secured to upper portion 604 to adjust the fit of cover 600 by using a fastening assembly, such as a hook and loop fastening assembly.

Referring to FIG. 7, the other fastening element, which is complementary to fastening element 524, and of which upper and lower portions are indicated, respectively, by arrows 704-1 and 704-2, may be secured or attached (e.g., by sewing or stitching) to the underside 708 of toe protective cover 600, for example, towards the rearward or open end 616 of cover 600. (Underside 708 which is adjacent exposed toes (or foot) 516 may also comprise materials which are softer and more comfortable compared to those materials present on outside or outer surface 712 of toe protective cover 600.) As shown in FIG. 7, upper portion 704-1 of the complementary fastening element is underneath fit adjusting strap 620. Like fastening element 524 shown in FIG. 5, complementary fastening element 704 secured or attached to underside 708 of cover 604 may be a continuous strip of material, or may be provided as a plurality of separate disconnected segments of sufficient number and length to provide adequate fastening capability when fastening element 524 is positioned opposite to and is pressed or joined to complementary fastening element 704, as well as the capability to be unfastened when toe protective cover 600 is to be removed. Like fastening element 524, complementary fastening element 704 may be either the "hook" material or "loop" material of the hook and loop fastening assembly, but is illustrated in the embodiment shown FIG. 7 as being the "loop" material.

FIGS. 8 and 9 show an embodiment of coupled anchor assembly 300 secured (e.g., embedded) in an arm, wrist, or hand cast, indicated generally as 800. (Although FIGS. 8 and 9 show an embodiment of coupled anchor assembly 300 secured to (e.g., embedded in) a left arm, wrist, or hand cast, assembly 300 may be similarly secured to (e.g., embedded in) a right arm, wrist, or hand cast 800.) Referring to FIG. 8, coupled anchor assembly 300 is positioned and secured between the main or rearward arm portion 804 and forward or hand portion 808 of cast 800. Coupled anchor assembly 300 is also shown in FIG. 8 as being positioned proximate or near the wrist of the patient as further shown in FIG. 8, the exposed thumb 812 of the patient projects outwardly from one opening, indicated as 816, in hand portion 808 of cast 800, while the patient's fingers, indicated as 820, project outwardly from a second opening, indicated as 824, also from hand portion 808. Like coupled anchor assembly 300 shown in FIG. 5, recess 224 of coupled anchor assembly 300 shown in FIG. 8 is also provided with one fastening element 524 of a protective cover fastening assembly, for example, the "hook" material or "loop" material of a hook and loop fastening assembly. Protective cover fastening assembly element 524 may also be a continuous strip of material, as shown in FIG. 8, but may also be provided as a plurality of disconnected segments of sufficient number and length to provide adequate fastening capability.

Referring to FIG. 9, a left-handed thumb and finger protective cover is provided, which is generally indicated as 900. The embodiment of thumb and finger protective cover 900 shown in FIG. 9 may comprise a main portion, indicated generally as 904, a thumb portion, indicated generally as 908, which is connected to main portion 904, and a finger portion, indicated generally as 912, which is also connected to main portion 904. (For a right-handed cast 900, a right-handed embodiment of thumb and finger protective cover 900 which is correspondingly configured may be used with a right-handed cast 800.) Main portion 904, thumb portion 908, and finger portion 912 may be made from a variety of materials (e.g., for comfort such as warmth, for protection such as from sunlight, UV ray, etc., for washability, etc.), may be formed in a variety of patterns or designs, etc. For example, like upper portion 604 of toe protective cover 600, main portion 904 of thumb and finger protective cover 900 may be made from, for example, a breathable woven textile yet water resistant/waterproof material, natural or synthetic fur or fur-like materials, leather, suede and synthetic suede, etc., may be decorated with gemstones, artwork, designs, logos, etc. Thumb portion 908 and finger portion 912 which are attached, joined or connected (e.g., sewn or stitched) to main portion 904 may be made from, for example, natural or synthetic knit or plain weave woven textile materials (e.g., to provide flexibility for the fingers and thumb to twist, grip, etc.), leather, suede and synthetic suede, etc., may also be decorated with gemstones, art, logos, etc. As indicated by generally by arrow 916, the other fastening element (which may be the same or similar to complementary fastening element 704 shown for cover 600), for example, either the "hook" material or "loop" material of the hook and loop fastening assembly which complementary to fastening element 524 may be secured or attached to the underside (not shown which may also comprise softer and more comfortable materials like underside 708) of main portion 904 of thumb and finger protective cover 900, for example, similar to how complementary fastening element 704 is secured to underside 708 of toe protective cover 700. Thumb and finger protective cover 900 may also be made in different sizes, may be provided in different configurations to fit left or right hands, etc. Like fastening element 524 shown in FIG. 8, complementary fastening element 916 secured or attached to underside of main portion 904 may be a continuous strip of material, or may be provided as a plurality of disconnected segments of sufficient number and length to provide adequate fastening capability when fastening element 524 is pressed or joined to element 916.

As also shown in FIG. 9, thumb and finger protective cover 900 may be provided with a fit adjusting strap 920 (e.g., the same or similar to fit adjusting strap 620 which may also provide additional decorative features) which allows the patient to tighten, or correspondingly loosen, the fit of cover 900 over coupled anchor assembly 300. Like decorative strap 620, decorative strap 920 may be releasably secured to main portion 904 of cover 900 by using a fastening assembly, such as a hook and loop fastening assembly. Also shown in FIG. 9 is a generally triangular shaped elastic insert 924 which may be incorporated into main portion 904 at one end 928 thereof, and which may extend underneath strap 920 to the juncture of main portion 904 and finger portion 912 and underneath a smaller generally triangular-shaped reinforcement piece 932. Elastic insert 924 allows cover 900 to stretch open and thus fit a variety of sizes of cast 800. Although not shown in FIG. 9, a similar second elastic insert 924 may also be used on the opposite (bottom) side of cover 900 to additionally aid in keeping cover 900 stretched open.

In operation, complementary fastening element 704 of toe protective cover 700, (or the fastening element 916 of thumb and finger protective cover 900), is joined with fastening element 524 to fasten cover 700 (or cover 900) to coupled anchor assembly 300, for example, by pressing complementary fastening element 704 (or 916) against fastening element 524. In the reverse operation, toe protective cover 700 (or thumb and finger protective cover 900) may be removed from coupled anchor assembly 300 by physically pulling the respective covers 700 (or 900), thus separating complementary fastening element 704 (or 916) from fastening element 524. The fastening and unfastening of elements 704 (or 916) from element 524 for securing (or removing) cover 700 (or 900) may readily accomplished by the patient and/or medical personnel as need.

An alternative embodiment the orthopedic cast cover anchor assembly is further illustrated in FIGS. 10 and 11. Referring to FIG. 10, this alternative embodiment of the orthopedic cast cover anchor assembly is indicated generally as 1100. Similar to assembly 100, assembly 1100 includes an elongated cast anchoring member in the form of, for example, a generally rectangular-shaped anchor band, strap, or strip 1104 which extends along a longitudinal axis, indicated by dashed line 1108, from a first end 1112 to a second end second end 1116. Like anchor strip 104, anchor strip 1104 also has a pair of spaced apart and opposing side edges 1120 and 1124 which extend from first end 112 to second end 116 and which may be generally parallel to each other. Like anchor strip 104, also extending alongside edge 1120 is a cast securing portion in the form of, for example, a relatively planar flange indicated generally as 1128. Like anchor strip 104, also extending alongside edge 1124 is a protective cover fastening and coupling portion indicated generally 1132.

Referring to FIG. 11, like flange 128, flange 1128 has formed therein, etc., as indicated generally as 1204, a plurality or multiplicity of perforations, holes, apertures, punctures, etc. Flange 1128 functions the same or similarly to flange 128 in enabling anchor strip 1104 to be secured to the orthopedic cast by, for example, permitting the cast forming material to pass or permeate through flange 1128. Similar to anchor strip 104, anchor strip protective cover fastening and coupling portion 1132 comprises an upper protective cover fastening portion, indicated generally as 1216. Like upper fastening portion 216, upper fastening portion 1216 has formed therein a recess, depression, indentation, etc., indicated generally as 1224, having a pair of spaced apart shoulders, indicated as 1228 and 1232. Like recess 224, recess 1224 may also receive one element of fastening system, for example, one element of a hook and loop fastening assembly which may be either the "hook" material, or the "loop" material. Also, fastening and coupling portion 1132 is provided with a slot (not shown) the same or similar to slot 236 at end 1116 and underneath recess 1224 and which is open at end 1116.

As shown in FIG. 10, as well as FIG. 11, where anchor assembly 1100 differs from anchor assembly 100 is in having the coupler member, indicated generally as 1136, being attached to or integral with end 1112 of anchor strip 1104. Coupler member 1136 also has one ribbed slot receivable and securable portion, indicated generally as 1140, which extends from end 1112 and which has an end segment 1316. Like ribbed portion 140 of coupler member 136, ribbed portion 1140 also has a plurality of generally oval or elliptical-shaped ribbed segments which protrude outwardly and orthogonally from a coupler member longitudinal axis (indicated by dashed 1324), and which also are laterally spaced apart along axis 324. Four such ribbed segments 1328-1, 1328-2, 1324-3, and 1328-4 are shown and indicated in FIG. 11 for ribbed portion 1140, although fewer or more ribbed segments than shown in FIG. 11 may also be used.

Ribbed portion 1140 functions similarly to ribbed portion 140 described above in coupling or uncoupling anchor strip 1104. For example, end segment 1316 of ribbed portion 1140 is first inserted into end of portion of the slot (as described above for end portion 348 of slot 236)) positioned and open at end 1116. The edges of ribbed segments 1328-1 through 1328-4 of ribbed portion 1140 slidably and frictionally engages the walls of this slot to keep anchor strip 1104 in coupled configuration (see FIG. 4). Like anchor strip 104 and coupler member 136, edges of ribbed segments 1328-1 through 1328-4 slidably and frictionally engage the walls of the slot of anchor strip 1104 so that anchor strip 1104 may remain in coupled configuration (see FIG. 4). Like coupled anchor assembly 300, a toe protective cover 600 (see FIGS. 5-7) or thumb and a hand protective cover 800 (see FIGS. 8 and 9) may be used with coupled anchor assembly 1100.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A product comprising an orthopedic cast cover kit comprising:
    at least one elongated cast anchoring member extending along a longitudinal axis from a first end to a second end and having:
        a pair of spaced apart and opposing side edges each extending from the first end to the second end of the at least one elongated cast anchoring member;
        a cast securing portion extending along one side edge from the first end to the second end of the at least one elongated cast anchoring member for securing the cast anchoring member to an orthopedic cast;
        an upper cover fastening portion extending along the other side edge from the first end to the second end of the at least one elongated cast anchoring member for releasably fastening a limb protective cover to the at least one elongated cast anchoring member;
        a lower coupler member receiving and securing slot extending underneath the upper fastening portion and having at least one coupler member receiving and securing portion positioned at at least one of the first end and the second end of the at least one elongated cast anchoring member; and
    at least one coupler member having at least one slot receivable and securable portion which may be received by the at least one coupler member receiving and securing slot portion;
    wherein when the at least one slot receivable and securable portion of the at least one coupler member is received by and secured within the at least one coupler member receiving and securing slot portion of the at least one cast anchoring member to form a coupled cast anchor assembly, the coupled cast anchor assembly is in a generally annular configuration; and
    at least one limb protective cover which can be releasably fastened to the upper fastening portion of the at least one cast anchoring member.

2. The kit of claim 1, wherein the upper cover fastening portion has one fastening element of a fastening assembly comprising a complementary pair of fastening elements, wherein the limb protective cover has an underside which is positioned adjacent an exposed limb, and wherein the other fastening element of the complementary pair of fastening elements is secured to the underside of the limb protective cover so that when the one fastening element of the upper cover fastening portion is positioned opposite the other fastening element secured to underside of the limb protective cover, the one fastening element of the upper cover fastening portion may be fastened to the other fastening element secured to underside of the limb protective cover.

3. The kit of claim 2, wherein the fastening assembly comprises a hook and loop fastening assembly having a hook element and a loop element, and wherein the one fastening element of the upper cover fastening portion is the hook element, and wherein the other fastening element secured to underside of the limb protective cover is the loop element.

4. The kit of claim 3, wherein one fastening element comprises one continuous hook element and wherein the other fastening element comprises one continuous loop element.

5. The kit of claim 4, wherein one fastening element comprises a plurality of disconnected hook elements and wherein the other fastening element comprises a plurality of disconnected loop elements.

6. The kit of claim 1, which comprises a plurality of elongated cast anchoring members, a plurality of coupler members, and a plurality of limb protective covers.

7. The kit of claim 1, wherein the limb protective covers comprise one or more of toe protective covers; or thumb and finger protective covers.

8. The kit of claim 1, wherein the cast securing portion comprises a perforated flange.

9. The kit of claim 1, wherein the at least one elongated cast anchoring member has one coupler member receiving and securing slot positioned at one of the first end and the second end of the at least one elongated cast anchoring member, and wherein the at least one coupler member has one slot receivable and securable portion, and wherein the one slot receivable and securable portion of the at least one coupler member is integral with the other of the first end and the second end of the at least one cast anchoring member.

10. The kit of claim 1, wherein the at least one elongated cast anchoring member has a pair of coupler member receiving and securing slot portions, one of the slot receiving and securing portions being positioned at each of the first end and the second end of the at least one elongated cast anchoring member, and wherein the at least one coupler member has a pair of slot receivable and securable portions, one of each of the slot receivable and securable portions of the at least one coupler member being received by each of the coupler member receiving and securing slot portions of the at least one cast anchoring member.

11. A device comprising an orthopedic cast cover anchor assembly comprising
an elongated cast anchoring member extending along a longitudinal axis from a first end to a second end and having:
a pair of spaced apart and opposing side edges each extending from the first end to the second end of the elongated cast anchoring member;
a cast securing portion extending along one side edge from the first end to the second end of the elongated cast anchoring member for securing the cast anchoring member to an orthopedic cast,
a cover fastening portion extending along the other side edge from the first end to the second end of the elongated cast anchoring member for releasably fastening a limb protective cover to the elongated cast anchoring member;
a coupler member receiving and securing slot at at least one of the first end and the second end of the cast anchoring member; and
a coupler member having at least one slot receivable and securable portion;
wherein when the at least one slot receivable and securable portion of the coupler member is received by and secured within the coupler member receiving and securing slot to form a coupled cast anchor assembly, the coupled cast anchor assembly is in a generally annular configuration.

12. The device of claim 11, wherein the coupler member has a longitudinal axis and wherein the at least one slot receivable and securable portion of the coupler member comprises at least one ribbed portion extending along the coupler member longitudinal axis, the at least one ribbed portion comprising a plurality of generally oval-shaped ribbed segments laterally spaced apart along the coupler member longitudinal axis and which extend orthogonally outwardly from the coupler member longitudinal axis, and wherein the coupler member receiving and securing slot comprises at least one wall which slidably engages the ribbed segments.

13. The device of claim 12, wherein a pair of adjacent ribbed segments are connected by a convex shaped connecting segment.

14. The device of claim 13, wherein the elongated cast anchoring member has one coupler member receiving and securing slot positioned at one of the first end and the second end of the elongated cast anchoring member, and wherein the coupler member has one slot receivable and securable portion which is integral with the other of the first end and the second end of the elongated cast anchoring member.

15. The device of claim 11, wherein the cover fastening portion comprises a recess which may receive one fastening element of a fastening assembly.

16. The device of claim 15, wherein the fastening assembly comprises a hook and loop fastening assembly having a hook element and a loop element, and wherein one of the hook and loop elements may be received by the recess.

17. The device of claim 11, wherein the cast securing portion comprises a perforated generally planar flange.

18. The device of claim 11, wherein the coupler member receiving and securing slot extends underneath the cover fastening portion.

19. A device comprising an orthopedic cast cover anchor assembly comprising
an elongated cast anchoring member extending along a longitudinal axis from a first end to a second end and having:
a pair of spaced apart and opposing side edges each extending from the first end to the second end of the elongated cast anchoring member;
a cast securing portion extending along one side edge from the first end to the second end of the elongated cast anchoring member for securing the elongated cast anchoring member to an orthopedic cast;
an upper cover fastening portion extending along the other side edge from the first end to the second end of the elongated cast anchoring member for releasably fastening a limb protective cover to the elongated cast anchoring member;
a lower coupler member receiving and securing slot extending underneath the upper fastening portion and having portions positioned at each of the first end and the second end of the elongated cast anchoring member; and
a coupler member having a first slot receivable and securable portion and a second slot receivable and securable portion;
wherein when the first slot receivable and securable portion of the coupler member is received by and secured within one portion of the lower coupler member receiving and securing slot positioned at the first end of the elongated cast anchoring member and wherein when the second slot receivable and securable portion of the coupler member is received by and secured within the other portion of the lower coupler member receiving and securing slot positioned at the second end of the elongated cast anchoring member to form a coupled cast anchor assembly, the coupled cast anchor assembly is in a generally annular configuration.

20. The device of claim 19, wherein the coupler member has a longitudinal axis and wherein each of the first and second slot receivable and securable portions of the coupler member comprise a plurality of generally oval-shaped ribbed segments laterally spaced apart along the coupler member longitudinal axis and which extend orthogonally outwardly from the coupler member longitudinal axis, and wherein the portions of the lower coupler member receiving and securing slot positioned at the first end and second end of the cast anchoring member each comprise at least one wall which slidably engages the ribbed segments of each of the first and second slot receivable and securable portions of the coupler member received by the respective portions of the lower coupler member receiving and securing slot.

21. The device of claim 20, wherein each pair of adjacent ribbed segments of each of the first and second slot receivable and securable portions of the coupler member are connected by a convex shaped connecting segment.

22. The device of claim 21, wherein the coupler member further comprises a central divider segment which is positioned between the first and second slot receivable and securable portions of the coupler member, which is connected to one of the ribbed segments of each of the first and second slot receivable and securable portions of the coupler member, and which is sized so as not to fit within the portions of the lower coupler member receiving and securing slot positioned at the first end and the second end of the cast anchoring member.

23. The device of claim 19, wherein the upper cover fastening portion comprises a recess which may receive one fastening element of a fastening assembly comprising a complementary pair of fastening elements.

24. The device of claim 23, wherein the fastening assembly comprises a hook and loop fastening assembly having a hook element and a loop element, and wherein one of the hook and loop elements may be received by the recess.

25. The device of claim 19, wherein the lower coupler member receiving and securing slot extends continuously from the first end to the second end of the elongated cast anchoring member.

26. The device of claim 19, wherein the lower coupler member receiving and securing slot comprises a first end portion positioned and open at the first end of the elongated cast anchoring member and a second end portion positioned and open at the second end of the elongated cast anchoring member, and wherein the first and second end portions of the lower coupler member receiving and securing slot are unconnected.

* * * * *